US00PP21556P3

(12) United States Plant Patent
Pinochet

(10) Patent No.: US PP21,556 P3
(45) Date of Patent: Dec. 7, 2010

(54) PLUM ALMOND TREE NAMED 'PAC 941'

(50) Latin Name: *Prunus cerasifera×Prunus dulcis*
Varietal Denomination: PAC 941

(75) Inventor: Jorge Pinochet, Barcelona (ES)

(73) Assignee: Agromillora Iberia, SA

( * ) Notice: Subject to any disclaimer, the term of this patent is extended or adjusted under 35 U.S.C. 154(b) by 59 days.

(21) Appl. No.: 12/321,289

(22) Filed: Jan. 15, 2009

(65) Prior Publication Data

US 2010/0095416 P1 Apr. 15, 2010

Related U.S. Application Data

(63) Continuation of application No. 12/250,738, filed on Oct. 14, 2008.

(51) Int. Cl.
*A01H 5/00* (2006.01)

(52) U.S. Cl. ..... Plt./180

(58) Field of Classification Search ..... Plt./155, Plt./180, 184
See application file for complete search history.

(56) References Cited

OTHER PUBLICATIONS

Moreno, M.A., et al, "Adesoto 101, A Plum Rootstock for Peaches and Other Stone Fruit" J. Am. Soc. Horticultural Science (1995), 30(6): 1314-1315; Alexandria, VA.

Agromillora Catalana, S.A., "Mariana GF-8/1" catalog entry (circa 1998), p. 3.

Brooks and Olmo, "Register of Fruit & Nut Varieties" (3rd Ed, 1997), pp. 606, 609.

Rom, R.C., and Carlson, R.F., "Rootstocks for Fruit Crops" (1987), Ch. 10, Okie, William R. "Plum Rootstocks" pp. 321-360; Wiley, NY.

*Primary Examiner*—Kent L Bell
(74) *Attorney, Agent, or Firm*—Mark D. Miller

(57) ABSTRACT

A new and distinct plum almond hybrid cultivar for rootstock use that originated as a pollinated seedling as provided. This new invention (cultivar) is particularly well suited for use as a plum, peach, nectarine, apricot and almond rootstock. It is found that this new invention (cultivar) exhibits good root anchorage as well as a significantly reduced tendency to form unwanted suckers.

1 Drawing Sheet

Plum Almond Tree Named 'PAC 941'
(*Prunus cerasifera×Prunus dulcis* Plum Almond Hybrid—Rootstock)

BACKGROUND OF THE NEW VARIETY

The original hybrid was discovered in Zaragoza, Spain and is thought to be a pollinated hybrid of the 'Myrobalan' plum (*Prunus cerasifera*) and almond (*Prunus dulcis*), both of unknown origin. Several original trees were found in a nursery in 1994 in Sabiñan, Zaragoza, observed and tested for nematodes and ease of propagation by wood cuttings resulting in the selection of one single tree, 'PAC 941', which became the experimental designation of the selection and afterwards the new cultivar. The cultivars of the parents are unknown.

SUMMARY OF THE INVENTION

In 1994, several seedlings having a similar growth pattern and morphology were discovered in a plum nursery in Sabiñan, Zaragoza, Spain. They differed in morphology at the same site and are thought to be a pollinated interspecific hybrid between plum and peach or plum and almond. The source of the seed that resulted in the production of the new cultivar of the present invention is not known but is thought to be local. Seven similar and distinct seedlings were observed propagated by cuttings in 1995 and evaluated against root-knot nematodes (*Meloidogyne* species) and lesion nematodes (*Pratylenchus vulnus*) in 1996. The most interesting trees from the nematode standpoint was chosen for further study. The rest were discarded. The selected trees was designated 'PAC 941'. In 1999, 'PAC 941' was introduced into the United States in Prosser, Wash. as Plum 'PAC 941'.

'PAC 941' was propagated in vitro from the original plant and evaluated for biotic and abiotic stress, and tested in field trials between 1997 and 2007 in Spain. It was found to possess horticutural characteristics (discussed hereinafter) that were superior to widely grown similar plum rootstocks such as 'Marianna 2624', 'Myrobalan 29C', 'Marianna GF-81' and 'Adesto 101'.

The new plum almond hybrid cultivar of the present invention was found to exhibit the following: (1) excellent root anchorage when compared to other peach and plum rootstocks; (2) a substantially less propensity to form suckers when compared to other plum rootstocks; (3) aptitude to serve as a plum, nectarine, peach, almond or apricot rootstock; and (4) excellent adaptation to limited soil conditions, especially water logging and calcareous soils (high lime content).

The root system extends more deeply and more vertically into the ground than 'Marianna 2624' and 'Adesto 101'. The lesser propensity to form suckers offers significant savings in labor. Its specter of compatibility with several Prunus species used as commercial varieties, mainly, peach, plum nectarine, almond and apricot, makes this cultivar a most interesting choice as a rootstock in sites where soil limitations do not allow, for example, peach cultivation with traditional peach or peach-almond rootstocks. Its outstanding adaptation to poor, heavy soils with high lime content (that cause iron chlorosis), offers a better production alternative for several Prunus species in limiting conditions and with a cost reduction in iron kelate applications. These characteristics make this cultivar ideal for replant situations. When compared with 'Marianna 2624' or 'Myrobalan 29C', the new cultivar does not form fruit.

The new cultivar is a standard diploid as are both *Prunus cerasifera* and *Prunus dulcis* as parents. The new cultivar has served well when grafted with the French prune variety 'Stanley' and Japanese plum (*Prunus salicina*) varieties 'Black Gold', 'Red Beaute', 'Golden Globe', 'Grand Rosa', and 'Son Gold'. The new cultivar has shown good compatibility with the nectarine (*Prunus persica*) varieties 'Summergrand', 'Big Top', and 'Alexandra' as well as with the almond varieties (*Prunus dulcis*) 'Moncayo', 'Desmayo Largueta', 'Butte', 'Nonpareil' and 'Monterey'.

The new cultivar (invention) has been reproduced at a commercial nursery, located in McMinnville, Oreg. by in vitro techniques on several occasions. Such propagations have confirmed that the characteristics of the new cultivar are stable and are reliably transmitted to subsequent generations.

BRIEF DESCRIPTION OF THE PHOTOGRAPH

The accompanying colored photograph displays terminal leaf tips along with mature leaves, both upper and lower surfaces. In addition, a section of older branch material is displayed. The trees of the new cultivar were grown near Bakersfield, Calif. Color designations are presented with reference to the "Dictionary of Color" by Maerz and Paul, First Edition (1930).

DETAILED DESCRIPTION

TREE

Size:
*Height.*—4-5 feet (121.92-152.4 cm).
*Width.*—4-5 feet (121.92-152.4 cm).
*Figure.*—Upright in form in open vase system.
Vigor: height of 4-5 feet reached during 2$^{nd}$ year.
Hardiness: hardy under climatic conditions in the Central San Joaquin Valley of California.
Productivity: none.
Bearing: non bearing.
Age of observed tree: 2 years old.

TRUNK

Size: medium.
Circumference: 4.5 inches (11.43 cm), at 8 inches (20.32 cm) above ground level
Texture: slightly rough.
Color: Teakwood Pinecone+ (15-C-9).
Lenticels: 0.5-1 per sq. cm.
*Length.*—0.15-0.25 inches (3.81-6.35 mm).
*Diameter.*—0.06-0.1 inches (1.5-2.5 mm).
*Texture.*—rough.
*Color.*—Old Roseleaf (7-J-3).

BRANCHES

Size: medium.
*Size over one year old.*—diameter of 2.5 inches (6.85 cm) at 10 inches (25.4 cm) above crotch.
*Crotch angle.*—approximately 32°.
Texture: nearly smooth.
Color: Whippet (15-L-10).
*Current Season.*—Piquant Gr. (20-K-6).
Internode Length: 1.5-2.5 inches (3.81-6.35 cm).
*Color as internodes mature.*—Caldera (7-L-12).

LEAVES

*Size.*—small to medium.
*Length.*—2.59-3.54 inches (6.58-8.99 cm).
*Width.*—1.15 inch (2.92 cm).
Form: ovate to lanceolate.
Base: elliptical.
Upper surface texture: smooth.
Lower surface texture: glabrous.
Apex: acute and often twisted sideways.
Color: Upper surface: Chrome Gr. MD$^{P}$ (23-H-12).
*Lower surface.*—Eden Gr. (20-L-9).
*Midvein.*—Lettuce Gr. (20-L-5).
Margin: serrate generally except at basal margins which are crenate and somewhat irregular.
Petiole:
*Length.*—0.64 inch (1.63 cm).
*Diameter.*—1 mm.
*Color.*—Lettuce Gr. (20-L-5).
Glands: none.
Stipules: none.

FLOWERS

Since the flowers are imperfect and cannot form fruit, there is no scientific reason for including them in the description of 'PAC 941'.

MAJOR USES

The major use of this invention is for rootstock for French prune variety 'Stanley', Japanese plum (*Prunus salcinia*) varieties 'Blackgold', 'Red Beaute', 'Golden Globe', 'Grand Rosa', and 'Son Gold'. In addition, this invention has demonstrated good compatibility with the nectarine and peach (*Prunus persica*) varieties 'Summer Grand', 'Big Top', and 'Alexandra', as well as the almond varieties (*Prunus dulcis*) 'Montayo', 'Desmayo Largueta', 'Butte', 'Monterey', and 'Nonpareil' and apricot varieties.

This invention shows some indication of some resistance to root-knot nematodes (*Meloidogyne* species), root lesion nematodes (*Pratylenchus vulnus*), and wet soils.

This invention appears limited to adaptation to heavy amounts of water (water logging) and calcareous soils.

This invention propagates well by in vitro culture techniques.

What is claimed is:

1. A new distinct cultivar of plum almond tree exhibiting the following combination of characteristics:

a. superior rooting anchorage when compared to 'Marianna 2624' (non patented in U.S.);
b. less propensity to form suckers than most plum rootstocks;
c. aptitude to serve well as a rootstock for plums, peaches, nectarines, almonds and apricots; and
d. outstanding adaptation to limiting soil conditions, especially water logging and calcareous soil.

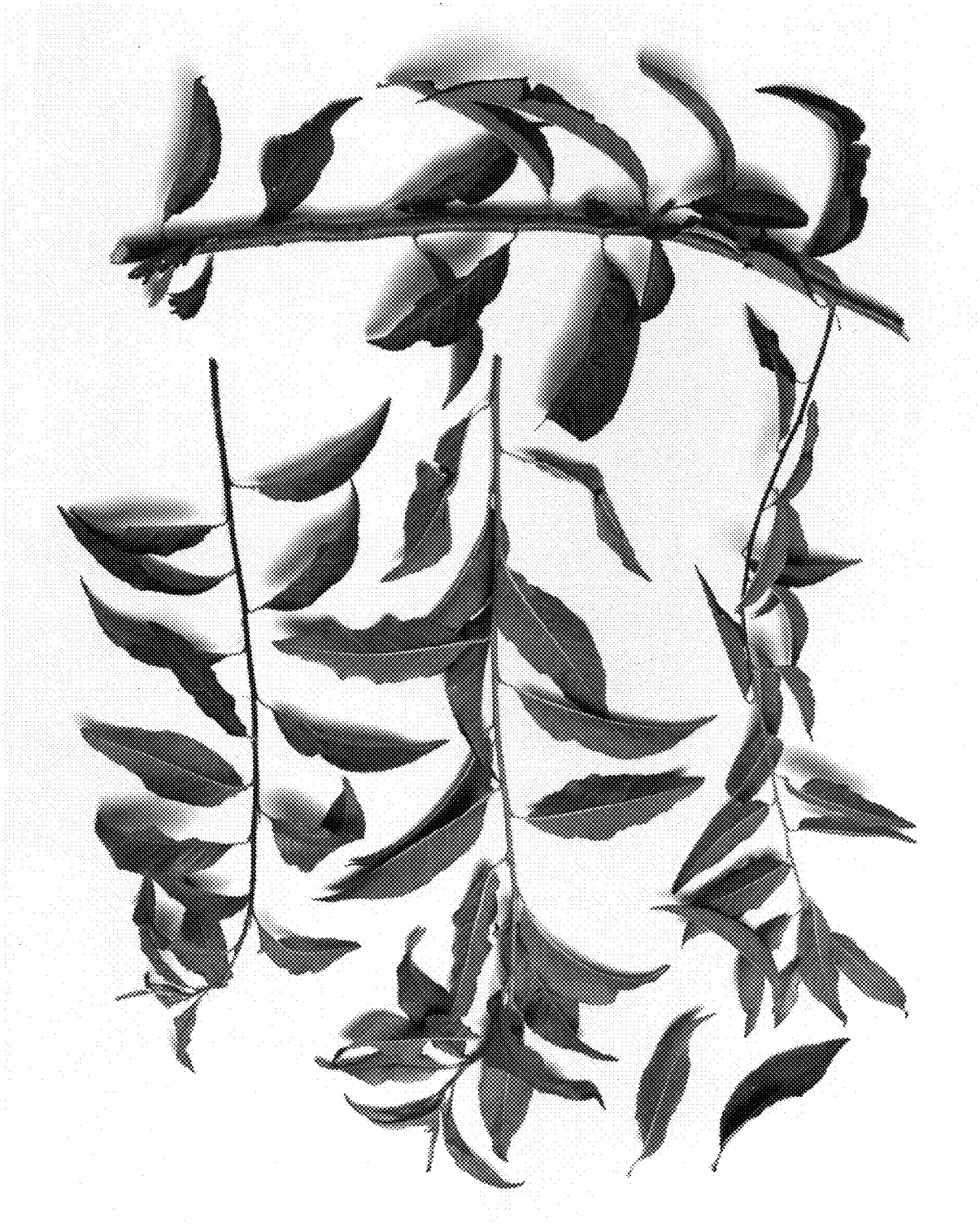

* * * * *